US006905678B2

(12) United States Patent
Havenga et al.

(10) Patent No.: US 6,905,678 B2
(45) Date of Patent: Jun. 14, 2005

(54) GENE DELIVERY VECTORS WITH CELL TYPE SPECIFICITY FOR MESENCHYMAL STEM CELLS

(75) Inventors: Menzo Jans Emco Havenga, Alphen a/d Rijn (NL); Abraham Bout, Moerkapelle (NL); Ronald Vogels, Linschoten (NL)

(73) Assignee: Crucell Holland B.V., Leiden (NL)

(*) Notice: Subject to any disclaimer, the term of this patent is extended or adjusted under 35 U.S.C. 154(b) by 164 days.

(21) Appl. No.: 10/010,645

(22) Filed: Nov. 13, 2001

(65) Prior Publication Data

US 2003/0049843 A1 Mar. 13, 2003

Related U.S. Application Data

(60) Provisional application No. 60/303,734, filed on Jul. 6, 2001.

(51) Int. Cl.[7] .................... A01N 63/00; C12N 15/00; C12N 5/00; C12N 21/06; C12N 15/63

(52) U.S. Cl. ................. 424/93.2; 424/93.21; 435/320.1; 435/325; 435/69.1; 435/455; 435/456; 514/44

(58) Field of Search ........................... 424/93.2, 93.21; 435/325, 69.1, 455, 456, 320.1, 235.1, 69.2, 440; 514/44

(56) References Cited

U.S. PATENT DOCUMENTS

| 6,127,525 A | * 10/2000 | Crystal et al. ......... 530/388.22 |
|---|---|---|
| 6,210,946 B1 | 4/2001 | Curiel et al. |
| 6,395,875 B1 | 5/2002 | Freimuth |
| 6,455,314 B1 | 9/2002 | Wickham et al. |
| 6,479,290 B1 | 11/2002 | Mehtali et al. |
| 2003/0053990 A1 | 3/2003 | Rabinowitz et al. |
| 2003/0077813 A1 | 4/2003 | Freimuth |

FOREIGN PATENT DOCUMENTS

| EP | 1 020 529 A2 | 7/2000 |
|---|---|---|
| EP | 1 067 888 A1 | 1/2001 |
| EP | 1 279 738 A1 | 1/2003 |
| JP | 02000157289 | * 6/2000 |
| WO | WO 00/52186 A1 | 9/2000 |

OTHER PUBLICATIONS

Kmiec, E.B. Gene Therapy. May–Jun., 1999. American Scientist, vol. 87, pp 240–247.*
Anderson, W.F, Human Gene Therapy. Apr., 1998. Nature, vol. 392, pp 25–30.*
Verma, I.M. and Somia, N. Gene Therapy—promises, problems and prospect. Sep., 1997. Nature, vol. 389, pp239–242.*
Russell, S.J. Replicating Vectors for Gene Therapy of Cancer: Risks, Limitations and Prospects, 1994. European J. of Cancer vol. 30(A), pp 1165–1171.*

Liu Q and Muruve DA. Molecular Basis of the inflammatory response to adenovirus vectors. Gene Therapy (2003) 10, 935–940.*
Stevenson et al., Human Adenovirus Serotypes 3 and 5 Bind to Two Different Cellular Receptors via the Fiber Head Domain, Journal of Virology, May 1995, pp. 2850–2857, vol. 69, No. 5.
Stevenson et al., Selective Targeting of Human Cells by a Chimeric Adenovirus Vector Containing a Modified Fiber Protein, Journal of Virology, Jun. 1997, pp. 4782–4790, vol. 71, No. 6.
Dmitriev et al., An Adenovirus with Genetically Modified Fibers Demonstrates Expanded Tropism via Utilization of a Coxsackievirus and Adenovirus Receptor–Independent Cell Entry Mechanism, Journal of Virology, Dec. 1998, pp. 9706–9713, vol. 72, No. 12.
Krasnykh et al., Generation of Recombinant Adenovirus Vectors with Modified Fibers for Altering Viral Tropism, Journal of Virology, Oct. 1996, pp. 6839–6846, vol. 70, No. 10.
Magnusson et al., Genetic Retargeting of Adenovirus: Novel Strategy Employing "Deknobbing" of the Fiber, Journal of Virology, Aug. 2001, pp. 7280–7289, vol. 75, No. 16.
Conget, P.A., et al., "Adenoviral–mediated gene transfer into ex vivo expanded human bone marrow mesenchymal progenitor cells," 28 Experimental Hematology 382–390 (2000).
Goossens, P.H., et al., "Infection Efficiency of Type 5 Adenoviral Vectors in Synovial Tissue Can Be Enhanced With a Type 16 Fiber," 44(3) Arthritis & Rheumatism 570–577 (Mar. 2001).
Havenga, M.J.E., et al., "Exploiting the Natural Diversity in Adenovirus Tropism for Therapy and Prevention of Disease," 76(9) Journal of Virology 4612–4620 (May 2002).
Havenga, M.J.E., et al., "Improved Adenovirus Vectors for Infection of Cardiovascular Tissue," 75(7) Journal of Virology 3335–3342 (Apr. 2001).
Marx, J.C., et al., "High–Efficiency Transduction and Long–Term Gene Expression with a Murine Stem Cell Retroviral Vector Encoding the Green Fluorescent Protein in Human Marrow Stromal Cells," 10 Human Gene Therapy 1163–1173 (May 1, 1999).
Olmsted–Davis, E.A., et al., "Use of a Chimeric Adenovirus Vector Enhances BMP2 Production and Bone Formation," 13 Human Gene Therapy 133–1347 (Jul. 20, 2002).

(Continued)

*Primary Examiner*—Gerry Leffers
*Assistant Examiner*—Maria Marvich
(74) *Attorney, Agent, or Firm*—TraskBritt

(57) ABSTRACT

Methods and associated materials for transducing mesenchymal stem cells with a desired nucleic acid. Mesenchymal stem cells are a recently discovered kind of stem cell for which suitable transfer vehicles are still desired. Typical gene delivery vehicles such as the adenoviruses or adeno associated viruses have no particular tropism for mesenchymal stem cells. Also disclosed is gene therapy using adenoviruses provided with tropism for mesenchymal stem cells.

12 Claims, 3 Drawing Sheets

OTHER PUBLICATIONS

Roelvink, P.W., et al., "Identification of a Conserved Receptor–Binding Site on the Fiber Proteins of CAR–Recognizing Adenovisidae," 286 Science 1568–1571 (Nov. 1999).

Roelvink, P.W., et al., "The Coxsackievirus–Adenovirus Receptor Protein Can Function as a Cellular Attachment Protein for Adenovirus Serotypes from Subgroups A, C, D, E, and F," 72(10) Journal of Virology 7909–7915 (Oct. 1998).

Turgeman, G., et al., "Bone Stem Cell Mediated Gene Therapy and Tissue Engineering," 15(7) Journal of Bone and Mineral Research S196 (Sep. 2000), Abstract.

Turgeman, G., et al., "Engineered human mesenchymal steam cells: a novel platform for skeletal cell mediated gene therapy," 3 J. Gene Med. 240–251 (2001).

Viggeswarapu, M., et al., "Adenoviral Delivery of LIM Mineralization Protein–1 Induces New–Bone Formation in Vitro and in Vivo," 83–A(3) The Journal of Bone & Joint Surgery 364–376 (Mar. 2001).

Yotnda, P., et al., "Efficient infection of primitive hematopoietic stem cells by modified adenovrus," 8(12) Gene Therapy 930–937 (Jun. 2001).

* cited by examiner-

GENE DELIVERY VECTORS WITH CELL TYPE SPECIFICITY FOR MESENCHYMAL STEM CELLS

CROSS REFERENCE TO RELATED APPLICATION

Under the provisions of 35 U.S.C. § 119(e), priority is claimed from U.S. Provisional Patent Application Ser. No. 60/303,734, filed Jul. 6, 2001, the entirety of which is hereby incorporated herein by this reference.

TECHNICAL FIELD

The present invention relates to methods and means for transducing mesenchymal stem cells with a desired nucleic acid. Mesenchymal stem cells are a recently discovered kind of stem cells for which suitable transfer vehicles are still desired. Typical gene delivery vehicles such as the generally used adenoviruses or adeno associated viruses have no particular tropism for mesenchymal stem cells as disclosed herein.

Thus, in particular the present invention relates to the field of gene therapy, more in particular to gene therapy using adenoviruses provided with tropism for mesenchymal stem cells.

BACKGROUND

In gene therapy, genetic information is delivered to a host cell in order to either correct (supplement) a genetic deficiency in the cell, or to inhibit an unwanted function in the cell, or to eliminate the host cell. Of course the genetic information can also be intended to provide the host cell with a wanted function, for instance to supply a secreted protein to treat other cells of the host, etc.

Thus, there are basically three different approaches in gene therapy, one directed towards compensating a deficiency present in a (mammalian) host; the second directed towards the removal or elimination of unwanted substances (organisms or cells) and the third towards providing a cell with a wanted function.

In order to provide cells with a gene (nucleic acid) of interest for any of the purposes identified above, a vehicle capable of delivering the gene to a host cell in a functional format is necessary. In certain instances transient expression (up to a number of weeks or somewhat longer) is desired, in others permanent transduction of a host cell seems necessary. In order to achieve these goals various vehicles are available. Retroviruses and adeno associated viruses are capable of integrating their genome (including a gene (nucleic acid) of interest) into the genome of a host cell, adenoviruses remain episomal. However, adenoviruses are better capable of infecting many kinds of cells, since retrovirus only infects certain specific cells. Combinations of different viruses (chimeric viruses) have been proposed to use the advantages of different kinds of viruses.

Of course, non-viral delivery systems are also available as are synthetic viruses, all of which can also be adapted to the specific target at hand. All of these systems may be applied in the hereinafter described invention.

It is known that stem cells are typically difficult to infect to a significant extent with the gene delivery vehicles of the prior art. If infection succeeds, functional expression, especially over a significant amount of time has been difficult to achieve. The infection of stem cells has been considered one of the more disappointing aspects of gene therapy.

DISCLOSURE OF THE INVENTION

The invention provides methods and means for delivering genes (nucleic acids of interest) to mesenchymal stem cells by providing gene delivery vehicles with a tropism for mesenchymal stem cells, typically in combination with a reduced tropism for other kinds of cells, in particular, liver cells.

Thus, the invention provides a nucleic acid delivery vehicle having at least a tissue tropism for mesenchymal stem cells and preferably having at least partially reduced tissue tropism for liver cells and other cells with which the gene delivery vehicle may come in contact in the host. Typically the vehicle according to the invention is provided with the tissue tropism by at least a part of a virus capsid (or envelope) or a functional derivative and/or analogue thereof. The capsid may comprise proteins, or functional parts, derivatives and/or analogues thereof from one or more viruses of the same species, but different subtypes or from different viruses. Preferably, at least one of the viruses is an adenovirus, typically an adenovirus of subgroup B.

Typically, at least one of the proteins derived from the capsid comprises a tissue tropism determining part of a fiber protein derived from a subgroup B adenovirus, in particular from an adenovirus of serotype 11, 16, 35 and/or 51 or a functional derivative and/or analogue thereof. Herein, we demonstrate that the gene delivery vehicles of the invention, provided with a tissue tropism determining part of an adenovirus type B fiber, have increased tropism for mesenchymal stem cells. A particular suitable tropism determining part can be derived from the fiber protein of adenovirus 16 ("Ad16"). It is preferred to use a whole fiber protein of an adenovirus comprising such a part of the fiber of Ad16.

We have found that chimeric adenoviruses are particularly suitable for targeting mesenchymal stem cells. Thus, the invention further includes a gene delivery vehicle according to the invention further comprising at least one protein derived from an adenovirus not belonging to subgroup B, or a functional part, derivative and/or analogue thereof. Preferably, the protein or a functional part, derivative and/or analogue thereof not derived from an adenovirus of subgroup B is derived from an adenovirus of subgroup C, preferably of adenovirus 5 for reasons described hereinafter. Also, the nucleic acid comprising the nucleic acid of interest (the gene) to be delivered is preferably of adenoviral origin, be it of one or more different adenoviruses.

Typically, the adenovirus derived nucleic acid encodes a fiber protein comprising at least a tissue tropism determining part of a subgroup B adenovirus fiber protein, in particular of a serotype 11, 16, 35 and/or 51, preferably of Ad16 or a functional derivative and/or analogue thereof. "Functional derivatives and analogues" when used herein are intended to include molecules based on those disclosed herein, be it chemically derived, theoretically derived, or experimentally designed to have the same function (in kind, but not necessarily in amount). This includes in the cases of nucleic acids and/or proteinaceous molecules, molecules having a high homology to the particular ones disclosed (both fragments and derivatives) and providing similar function. In some embodiments, the nucleic acid delivery vehicle must not replicate in target cells. In such instances, it is preferred that the adenovirus nucleic acid is a modified nucleic acid such that the capacity of the adenovirus nucleic acid to replicate in a target cell has been reduced or disabled, preferably through a deletion of at least part of the adenoviral E1-region.

In order to achieve expression of the gene of interest over a significant amount of time, it is preferred to provide a gene delivery vehicle capable of avoiding an immune response to a certain extent. Therefore, the invention includes a vehicle according to the invention, wherein the adenovirus nucleic acid is a modified nucleic acid such that the capacity of a host immune system to mount an immune response against adenovirus proteins encoded by the adenovirus nucleic acid has been reduced or disabled, preferably through a deletion of adenovirus E2A and/or at least part of the E4-region.

The invention also provides a vehicle according to the invention, including a minimal adenovirus vector or an Ad/AAV chimeric vector.

The invention further provides methods for producing a vehicle according to the invention, comprising providing a cell with means for the assembly of the vehicle, wherein the means includes a means for the production of an adenovirus fiber protein, wherein the fiber protein comprises at least a tissue tropism determining part of a subgroup B adenovirus, in particular a serotype 11, 16, 35 and/or 51 adenovirus fiber protein or a functional derivative and/or analogue thereof. Further details are given in the detailed description.

The invention further provides a cell for producing a vehicle according to the invention, the cell comprising means for the assembly of the vehicle, wherein the means includes a means for producing an adenoviral fiber protein, wherein the fiber protein comprises at least a tissue tropism determining part of a subgroup B adenovirus fiber protein, in particular, a serotype 11, 16, 35 and/or 51 adenovirus or a functional derivative and/or analogue thereof, preferably the cell is or is derived from a PER.C6 cell (ECACC deposit number 96022940). Further details are given in the detailed description.

DETAILED DESCRIPTION

Figure 1:
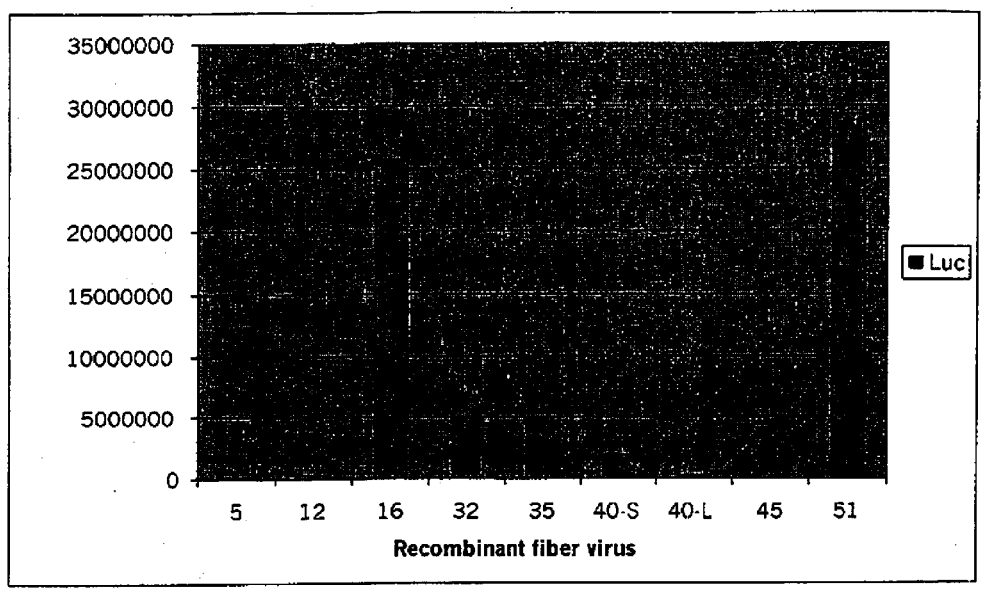
FIG. 1: Screening the fiber chimeric viruses for the presence of viruses that are better suited for transduction of primary human mesenchymal stem cells. The dose used is 1000 virus particles per cell. Luciferase activity is expressed (the y-axis) in relative light units ("RLU").

For the sake of brevity, the present invention is explained in more detail based on one of its embodiments relating to gene delivery vehicles based on adenoviruses.

For the purpose of gene therapy, adenoviruses have been proposed as suitable vehicles to deliver genes to the host. Gene-transfer vectors derived from adenoviruses (so-called adenoviral vectors) have a number of features that make them particularly useful for gene transfer. 1) the biology of the adenoviruses is characterized in detail, 2) the adenovirus is not associated with severe human pathology, 3) the virus is extremely efficient in introducing its DNA into the host cell, 4) the virus can infect a wide variety of cells and has a broad host-range, 5) the virus can be produced at high virus titers in large quantities, and 6) the virus can be rendered replication defective by deletion of the early-region 1 (E1) of the viral genome (Brody et al., 1994).

However, there are still drawbacks associated with the use of adenoviral vectors especially the well-investigated serotypes of subgroup C adenoviruses. These serotypes require the presence of the Coxsackie adenovirus receptor (CAR) on cells for successful infection. Although this protein is expressed by many cells and established cell lines, this protein is absent on many other primary cells and cell lines making the latter cells difficult to infect with serotypes 1, 2, 5, and 6.

The adenovirus genome is a linear double-stranded DNA molecule of approximately 36,000 base pairs. The adenovirus DNA contains identical Inverted Terminal Repeats ("ITRs") of approximately 90–140 base pairs ("bp") with the exact length depending on the serotype. The viral origins of replication are within the ITRs exactly at the genome ends.

Most adenoviral vectors currently used in gene therapy have a deletion in the E1 region, where novel genetic information can be introduced. The E1 deletion renders the recombinant virus replication defective (Levrero et al 1991). It has been demonstrated extensively that recombinant adenovirus, in particular Ad5 is suitable for efficient transfer of genes in vivo to the liver, the airway epithelium and solid tumors in animal models and human xenografts in immunodeficient mice (Bout 1996; Blaese et al 1995). Thus, preferred methods for in vivo gene transfer into target cells make use of adenoviral vectors as gene delivery vehicles.

At present, six different subgroups of human adenoviruses have been proposed which in total encompasses 51 distinct adenovirus serotypes. Besides these human adenoviruses an extensive number of animal adenoviruses have been identified (see Ishibashi et al 1983).

A serotype is defined on the basis of its immunological distinctiveness as determined by quantitative neutralization with animal antisera (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al 1991). The nine serotypes identified last (42–51) were isolated for the first time from HIV-infected patients (Hierholzer et al 1988; Schnurr et al 1993; De Jong et al 1999). For reasons not well understood, most of such immuno-compromised patients shed adenoviruses that were rarely or never isolated from immuno-competent individuals (Hierholzer et al 1988 and 1992; Khoo et al 1995; De Jong et al 1999).

The adenovirus Ad5 ("Ad5") is most widely used for gene therapy purposes. Similar to serotypes 2, 4 and 7, Ad5 has a natural affiliation towards lung epithelia and other respiratory tissues. In contrast, it is known that, for instance, serotypes 40 and 41 have a natural affiliation towards the gastrointestinal tract. For a detailed overview of the disease association of the different adenovirus serotypes, see Table 1. The natural affiliation of a given serotype towards a specific organ can either be due to a difference in the route of infection (i.e., make use of different receptor molecules or internalization pathways). However, it can also be due to the fact that a serotype can infect many tissues/organs, but it can only replicate in a particular organ or organs because of the requirement of certain cellular factors for replication and hence clinical disease. At present, it is unknown which of these mechanisms is responsible for the observed differences in human disease association. However, it is known that different adenovirus serotypes can bind to different receptors due to sequence dissimilarity of the capsid proteins i.e. hexon, penton, and fiber protein. For instance, it has been shown that adenoviruses of subgroup C such as Ad2, and Ad5 bind to different receptors as compared to adenoviruses from subgroup B such as Ad3 (Defer et al, 1990). Likewise, it was demonstrated that receptor specificity could be altered by exchanging the Ad3 with the Ad5 knob protein, and vice versa (Krasnykh et al 1996; Stevenson et al 1995 and 1997).

The present invention makes use of the observation that different adenovirus serotypes have different human disease associations which might be the result of differences in cellular host range which in turn might be the result of differences in capsid proteins, in particular the fiber protein.

The invention also provides a library of adenoviruses in which the sequence encoding for the fiber protein from alternative serotypes has been cloned into an adenovirus serotype 5 backbone thereby generating a chimeric adenovirus. This chimeric adenovirus thus has the host range of the adenovirus serotype of which the fiber sequence was cloned whereas all other aspects are derived from Ad5.

A gene of interest can also be inserted at, for instance, the site of E1 of the original adenovirus from which the vector is derived. In this manner, the chimeric adenovirus to be produced can be adapted to the requirements and needs of certain hosts in need of gene therapy for certain disorders. Naturally, to enable production of a chimeric adenovirus, a packaging cell will generally be needed in order to produce sufficient amount of safe chimeric adenoviruses.

The invention provides the means to produce the chimeric virus. Typically, one does not want an adenovirus batch to be administered to a host cell which contains replication competent adenovirus, although this is not always true. In general, therefore, it is desired to omit a number of genes (but at least one) from the adenoviral genome on the vector encoding the chimeric virus and to supply these genes in the genome of the cell in which the vector is brought to produce chimeric adenovirus. Such a cell is usually called a "packaging cell". The invention thus also provides a packaging cell for producing a chimeric adenovirus according to the invention, comprising in trans all elements necessary for adenovirus production not present on the adenoviral vector according to the invention. Typically, vector and packaging cells have to be adapted to one another in that they have all the necessary elements, but that they do not have overlapping elements which lead to replication competent virus by recombination.

In the human body, circulating blood cells survive for a predetermined period which, depending on the cell type can vary from hours to months. Therefore, there is a continuous need for red cells, platelets, lymphocytes, monocytes, and granulocytes. These cell pools are kept at a constant level through division and differentiation of hemopoietic stem cells (HSCs) derived from bone marrow. One of the features of HSCs is that they not adhere to plastic culture dishes under ex vivo culture conditions. Besides HSC, in recent years another stem-cell like cell has been identified in bone marrow which is of non-hemopoietic origin and which does adhere to plastic support. This stem cell-like cell is of mesenchymal origin and is therefore designated as mesenchymal stem cells or bone marrow stromal cells or MSCs. Many attributes of MSCs remain to be determined but their multipotentiality as demonstrated by the observations that MSCs can differentiate into osteoclasts, chondroblasts, fibroblasts, adipocytes and myoblasts (reviewed: Prockop et al 1997). Although HSCs and MSCs can be isolated from bone marrow, only the latter can be derived from other tissues such as skeletal muscle (Jackson et al 1999), liver (Crosbie et al 1999), and brain (Bjornson et al 1999). MSCs' pluripotency was further emphasized by the observation that MSCs derived from brain were capable of producing a variety of blood cell types including myeloid and lymphoid cells (Bjornson et al 1999). Like HSCs, the MSCs are being explored as vehicles for cell-, and gene therapy.

MSCs are relatively easy to obtain from small bone marrow aspirates under local anesthesia and are easy to culture under ex vivo conditions without losing their stem cell characteristics. Applications of MSCs for therapeutic interventions are both ex vivo, in the field of tissue engineering, as well as in vivo for treatment of acquired or congenital diseases. One illustrative example is to isolate MSCs from the bone marrow of patients afflicted with degenerative arthritis, expand the cells in culture, genetically modify the cells such that they express factors that interfere with, for instance, synoviocyte proliferation or inflammation, and then transplant the cells directly into the afflicted joints. Non-limiting examples of genes which interfere either with synoviocyte proliferation or inflammation is IL-10 (Dechanet et al 1995) or soluble VCAM-1 (Chen et al 1995).

Another application is the implantation of MSCs genetically modified to express stimulators of bone regeneration. An illustrative example of such genes is bone morphogenesis protein-2 ("BMP-2") or LIM mineralization protein-1 ("LMP-1") (Lou et al 1999, Boden et al 2000). These genetically modified MSCs are subsequently transplanted locally to induce bone formation. Alternatively, the cells are cultured ex vivo in a bio-reactor on a collagen scaffold to form artificial bone that can be surgically transplanted.

Locally injected MSCs were shown to promote repair of surgical incisions in the knee cartilage of rabbits, and MSCs in ceramic beads were shown to promote bone healing in an animal model (Goldberg et al 1994, Bruder et al 1994, Wakitani et al 1994). The same strategy can be applied to treat, for instance, multiple sclerosis. Here, autologous MSCs are genetically modified to express dystrophin before transplantation into striated muscle. Another example is to treat heart failure in which case MSCs expressing angiogenic inducing factors are transplanted in ischemic regions of a diseased heart. In the latter case genes such as nitric oxide synthase (NOS1–3), vascular endothelial growth factor (VEGF), or C-naturetic peptide (CNP) can be used.

Another illustrative example of an application of MSCs is to infuse MSCs systemically after they have been genetically modified to express secreted proteins. The MSCs home at different places in the body, secreting a therapeutic protein that exerts its function at specific (distant) sites. Non-limiting examples of interesting genes are Factor VIII, Factor IX, or mutant genes for β-glucocerebrosidase, erythropoietin ("EPO"), α-L-iduronidase, iduronate sulphatase, N-sulphatase, N-acetyl α-D-glucosaminidase, α-glucosamine-N-acetyltransferase, N-acetyl-α-D-glucosaminide-6-sulphatase, Galactosamine-6 sulphate sulphatase, β-galactosidase, N-acetyl-alactosamine-4-sulphatase, acid ceraminidase, acid sphingomyelinase, galactocerebroside β-galactosidase, arylsuphatase A, adenosine deaminase, α-L-fucosidase growth factors such as the interleukin family, angiogenesis stimulating or inhibiting factors such as the nitric oxide synthases (NOS1–3), vascular endothelial growth factors ("VEGF"), Angiostatin 1–7. Besides the direct infusion of genetically modified MSCs the cells can be encapsulated in inert material that allows the diffusion of proteins, but not the cells. At least for Factor IX, the feasibility of this approach was shown in immunodeficient mice transplanted with human MSCs. These mice expressed Factor IX for at least 8 months after systemic infusion.

One major advantage of MSCs over HSCs is that MSCs can be cultured to large numbers under ex vivo conditions without the loss of multipotency. The latter indicates that the abovementioned strategies can be applied to patients without the need for marrow ablative conditioning simply because large numbers of genetically modified cells can be infused. The examples described indicate that MSCs are of interest for many different therapeutic strategies and therefore genetic modification of this cell type is of considerable importance. For many applications, transient expression of exogenous genes is sufficient to trigger the MSCs to differentiate or to express periodically secreted proteins. Transient expression is sufficient if a process needs to be triggered (e.g., angiogenesis, chondrogenesis, bone formation). For other applications, sustained expression is necessary i.e. protein secretion to elevate protein deficiency (Factor VIII, Factor IX, sugar reducing enzymes etc). For all applications, adenoviruses as gene delivery vehicle can be used, since an adenovirus can be engineered to either or not integrate into the host cell genome (Concalves et al; 2000).

Alternative strategies to obtain integration and thus long-term expression have been published (Feng et al 1997; Zheng et al 2000). In these studies, an adenovirus is used to deliver an integrating vector (retrovirus) by cloning the retrovirus genome into the adenovirus genome. To identify an adenovirus which efficiently transduces MSCs provides clinical applications of any of the above mentioned strategies. Therefore, it is important to understand the molecular basis of adenovirus binding and internalization. For this reason, the steps involved in adenovirus binding as has been elucidated at present for Ad5 will be described.

The initial step for successful infection is binding of the adenovirus to its target cell, a process mediated through fiber protein. The fiber protein has a trimeric structure (Stouten et al 1992) with different lengths depending on the virus serotype (Signas et al 1985; Kidd et al 1993). Different serotypes have polypeptides with structurally similar N and C termini, but different middle stem regions. N-terminally, the first 30 amino acids are involved in anchoring of the fiber to the penton base (Chroboczek et al 1995), especially the conserved FNPVYP (SEQ ID NO:1) region in the tail (Arnberg et al 1997). The C-terminus, or knob, is responsible for initial interaction with the cellular adenovirus receptor. After this initial binding, secondary binding between the capsid penton base and cell-surface integrins is proposed to lead to internalization of viral particles in coated pits and endocytosis (Morgan et al 1969; Svensson et al 1984; Varga et al 1992; Greber et al 1993; Wickham et al 1995). Integrins are αβ-heterodimers of which at least 14α-subunits and 8β-sububits have been identified (Hynes et al 1992). The array of integrins expressed in cells is complex and will vary between cell types and cellular environment. Although the knob contains some conserved regions, between serotypes, knob proteins show a high degree of variability, indicating that different adenovirus receptors might exist. For instance, it has been demonstrated that adenoviruses of subgroup C (Ad2, Ad5) and adenoviruses of subgroup B (Ad3) bind to different receptors (Defer et al 1990). By using baculovirus produced soluble CAR as well as Ad5 knob protein, Roelvink et al (1998) concluded via interference studies that all adenovirus serotypes, except serotypes of subgroup B, enter cells via CAR.

Besides the involvement in cell binding, the fiber protein also contains the type specific γ-antigen, which together with the ε-antigen of the hexon determines the serotype specificity. The γ-antigen is localized on the fiber and it is known that it consists of 17 amino acids. The anti-fiber antibodies of the host are therefore directed to the trimeric structure of the knob. To obtain re-directed infection of recombinant Ad5, several approaches have been or still are under investigation. Wickham et al (1993 and 1995) have altered the RGD (Arg Gly Asp) motif in the penton base which is believed to be responsible for $\alpha_v\beta_3$ and/or $\alpha_v\beta_5$ integrin binding to the penton base. They have replaced this RGD motif by another peptide motif that is specific for the $\alpha_4\beta_1$ receptor. In this way, targeting of the adenovirus to a specific target cell could be accomplished. Krasnykh et al (1998) have made use of the HI loop available in the knob. This loop is, based on X-ray crystallographics, located on the outside of the knob trimeric structure and therefore is thought not to contribute to the intramolecular interactions in the knob. Insertion of a FLAG coding sequence into the HI loop resulted in targeting of the adenovirus to target cells by using antibodies which recognize both the FLAG epitope and a cellular receptor (Krasnykh et al 1998). However, complete CAR independent infection was not observed.

The present invention provides a method and means by which an adenovirus can infect primary human mesenchymal stem cells. Therefore, in one embodiment, the generation of chimeric adenoviruses based on Ad5 with modified fiber genes is described. For this purpose, two or three plasmids, which together contain the complete Ad5 genome, were constructed. From one of these plasmids the DNA encoding the Ad5 fiber protein was removed and replaced by linker DNA sequences that facilitate easy cloning. The plasmid in which the native Ad5 fiber sequence was partially removed subsequently served as template for the insertion of DNA encoding for fiber protein derived from different adenovirus serotypes (human or animal). The DNAs derived from the different serotypes were obtained using the polymerase chain reaction technique in combination with (degenerate) oligo-nucleotides. At the former E1 location in the genome of Ad5, any gene of interest can be cloned. A single transfection procedure of the two or three plasmids together resulted in the formation of a recombinant, fiber chimeric adenovirus. Although successful introduction of changes in the Ad5 fiber and penton-base have been reported by others, the complex structure of knob and the limited knowledge of the precise amino acids interacting with CAR render such targeting approaches laborious and difficult.

To overcome the limitations described above we preferably used pre-existing adenovirus fibers to maximize the chance of obtaining recombinant adenovirus which can normally assemble in the nucleus of a producer cell and which can be produced on pre-existing packaging cells. By generating a chimeric Ad5 based fiber library containing fiber proteins of all other human adenovirus serotypes, we have developed a technology which enables rapid screening for a recombinant adenoviral vector with preferred infection characteristics for primary human mesenchymal stem cells.

In one aspect, the invention describes the construction and use of plasmids consisting of distinct parts of Ad5 in which the gene encoding for fiber protein has been replaced with DNA derived from alternative human or animal serotypes. This set of constructs, in total encompassing the complete adenovirus genome, allows for the construction of unique chimeric adenoviruses customized for transduction of particular cell types or organ(s). Also, in this part of the invention means and methods to propagate, produce, and purify fiber chimeric adenoviruses is described.

In another aspect of the invention, chimeric viruses are described which have preferred infection characteristics in human mesenchymal stem cells. The adenoviral vectors preferably are derived from subgroup B adenoviruses or contain at least a functional part of the fiber protein from an adenovirus from subgroup B comprising at least the binding moiety of the fiber protein. In a further preferred embodiment the adenoviral vectors are chimeric vectors based on Ad5 and contain at least a functional part of the fiber protein from adenovirus type 16, 35, or 51. It is to be understood that in all embodiments, the adenoviral vectors may be derived from the serotype having the desired properties or that the adenoviral vector is based on an adenovirus from one serotype and contains the sequences comprising the desired functions of another serotype, these sequences replacing the native sequences in the serotype.

In another aspect of the invention, the chimeric adenoviruses may, but need not, contain deletions in the E1 region and insertions of heterologous genes linked either or not to a promoter. Furthermore, chimeric adenoviruses may, or may not, contain deletions in the E3 region and insertions of heterologous genes linked to a promoter. Furthermore, chimeric adenoviruses may, or may not, contain deletions in the E2 and/or E4 region and insertions of heterologous genes linked to a promoter. In the latter case, E2 and/or E4 complementing cell lines are required to generate recombinant adenoviruses.

The invention is further explained by use of the following illustrative Examples.

EXAMPLES

Example I

Generation of Ad5 Genomic Plasmid Clones

The complete genome of Ad5 has been cloned into various plasmids or cosmids to allow easy modification of parts of the Ad5 genome, while still retaining the capability to produce recombinant virus. For this purpose the following plasmids were generated:

1. pBr/Ad.Bam-rITR (ECACC deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent *E.coli* DH5a (Life Techn.) and analysis of ampiciline resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. The missing G residue is complemented by the other ITR during replication.

2. pBr/Ad.Sal-rITR (ECACC deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

3. pBr/Ad.Cla-Bam (ECACC deposit P97082117)

wt Adeno type 5 DNA was digested with ClaI and BamHI, and the 20.6 kb fragment was isolated from gel by electroelution. pBr322 was digested with the same enzymes and purified from agarose gel by Geneclean. Both fragments were ligated and transformed into competent DH5a. The resulting clone pBr/Ad.Cla-Bam was analysed by restriction enzyme digestion and shown to contain an insert with adenovirus sequences from bp 919 to 21566.

4. pBr/Ad.AflII-Bam (ECACC deposit P97082114)

Clone pBr/Ad.Cla-Bam was linearized with EcoRI (in pBr322) and partially digested with AflII. After heat inactivation of AflII for 20' at 65° C. the fragment ends were filled in with Klenow enzyme. The DNA was then ligated to a blunt double stranded oligo linker containing a PacI site (5'-AATTGTC<u>TTAATTAA</u>CCGCTTAA-3') (SEQ ID NO:2). This linker was made by annealing the following two oligonucleotides: 5'-AATTGTCTTAATTAACCGC-3' (SEQ ID NO:3) and 5'-AATTGCGGTTAATTAAGAC-3' (SEQ ID NO:4), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5a. One clone that was found to contain the PacI site and that had retained the large adeno fragment was selected and sequenced at the 5' end to verify correct insertion of the PacI linker in the (lost) AflII site.

5. pBr/Ad.Bam-rITRpac#2 (ECACC deposit P97082120) and pBr/Ad.Bam-rITR#8 (ECACC deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and resuspended in a smaller volume of TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10' or 15'. The 10' or 15' treated pBr/Ad.Bam-rITR samples were then ligated to the above described blunted PacI linkers (See pBr/Ad.AflII-Bam). Ligations were purified by precipitation, digested with excess PacI and separated from the linkers on an LMP agarose gel. After religation, DNAs were transformed into competent DH5a and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using 1 phage packaging extracts (Stratagene) according to the manufacturer's protocol. After infection into host bacteria, colonies were grown on plates and analyzed for presence of the complete insert. pWE/Ad.AFIII-rITR contains all adenovirus type 5 sequences from bp 3534 (AflII site) up to and including the right ITR (missing the most 3' G residue).

pBr/Ad.lITR-Sal(9.4) (ECACC deposit P97082115)

Adeno 5 wt DNA was treated with Klenow enzyme in the presence of excess dNTPs and subsequently digested with SalI. Two of the resulting fragments, designated left ITR-Sal(9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.lITR-Sal(16.7) (ECACC deposit P97082118)

pBr/Ad.lITR-Sal(9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenovirus sequences from 9462–16746 was isolated in LMP agarose gel and ligated to the SalI-digested pBr/Ad.lITR-Sal(9.4) vector fragment.

pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged.

First, a PCR fragment was generated from pZipΔMo+ PyF101 (N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:5) and LTR-2: 5'-GCG GAT CCT TCG AAC CAT GGT AAG CTT GGT ACC GCT AGC GTT AAC CGG GCG ACT CAG TCA ATC G-3' (SEQ ID NO:6). Pwo DNA polymerase (Boehringer Mannheim) was used according to manufacturers protocol with the following temperature cycles: once 5' at 95° C.; 3' at 55° C.; and 1' at 72° C., and 30 cycles of 1' at 95° C., 1' at 60° C., 1' at 72° C., followed by once 10' at 72° C. The PCR product was then digested with BamHI and ligated into pMLP10 (Levrero et al 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al 1990) using the following primers: HSA1, 5'-GCG CCA CCA TGG GCA GAG CGA TGG TGG C-3' (SEQ ID NO:7) and HSA2, 5'-GTT AGA TCT AAG CTT GTC GAC ATC GAT CTA CTA ACA GTA GAG ATG TAG AA-3' (SEQ ID NO:8). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI (blunt) fragment and cloned into the 3.5 kb NcoI(sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP.

Generation of Recombinant Adenoviruses

To generate E1 deleted recombinant adenoviruses with the new plasmid-based system, the following constructs are prepared:

a) An adapter construct containing the expression cassette with the gene of interest linearized with a restriction enzyme that cuts at the 3' side of the overlapping adenoviral genome fragment, preferably not containing any pBr322 vector sequences, and
b) A complementing adenoviral genome construct pWE/Ad.AflII-rITR digested with PacI.

These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct.

Alternatively, instead of pWE/Ad.AflII-rITR other fragments can be used, e.g., pBr/Ad.Cla-Bam digested with EcoRI and BamHI or pBr/Ad.AFIII-BamHI digested with PacI and BamHI can be combined with pBr/Ad.Sal-rITR digested with SalI. In this case, three plasmids are combined and two homologous recombinations are needed to obtain a recombinant adenovirus. It is to be understood that those skilled in the art may use other combinations of adapter and complementing plasmids without departing from the present invention.

A general protocol as outlined below and meant as a non-limiting example of the present invention has been performed to produce several recombinant adenoviruses using various adapter plasmids and the Ad.AflII-rITR fragment. Adenovirus packaging cells (PER.C6) were seeded in 25 cm$^2$ flasks and the next day when they were at ~80% confluency, transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AFIII- rITR (or 2 µg of all three plasmids for the double homologous recombination) are used. Under these conditions transient transfection efficiencies of ~50% (48 hrs post transfection) are obtained as determined with control transfections using a pAd/CMV-LacZ adapter. Two days later, cells are passaged to 80 cm$^2$ flasks and further cultured. Approximately five (for the single homologous recombination) to eleven days (for the double homologous recombination) later a cytopathogenic effect (CPE) is seen, indicating that functional adenovirus has formed. Cells and medium are harvested upon full CPE and recombinant virus is released by freeze-thawing. An extra amplification step in 80 cm$^2$ flasks is routinely performed to increase the yield since at the initial stage the titers are found to be variable despite the occurrence of full CPE. After amplification, viruses are harvested and plaque purified on PER.C6 cells. Individual plaques are tested for viruses with active transgenes.

Besides replacements in the E1 region it is possible to delete or replace (part of) the E3 region in the adenovirus because E3 functions are not necessary for the replication, packaging and infection of the (recombinant) virus. This creates the opportunity to use a larger insert or to insert more than one gene without exceeding the maximum package size (approximately 105% of wt genome length). This can be done, e.g., by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and pA sequences, leaving more space for coding sequences.

To this end, the 2.7 kb EcoRI fragment from wt Ad5 containing the 5' part of the E3 region was cloned into the EcoRI site of pBluescript (KS$^-$) (Stratagene). Next, the HindIII site in the polylinker was removed by digestion with EcoRV and HincII and subsequent religation. The resulting clone pBS.Eco-Eco/ad5DHIII was used to delete the gp 19K coding region. Primers 1 (5'-GGG TAT TAG GCC AAAGG CGC A-3') (SEQ ID NO:9) and 2 (5'-GAT CCC ATG GAA GCT TGG GTG GCG ACC CCA GCG-3') (SEQ ID NO:10) were used to amplify a sequence from pBS.Eco-Eco/Ad5DHIII corresponding to sequences 28511 to 28734 in wt Ad5 DNA. Primers 3 (5'-GAT CCC ATG GGG ATC CTT TAC TAA GTT ACA AAG CTA-3' (SEQ ID NO:11)) and 4 (5'-GTC GCT GTA GTT GGA CTG G-3' (SEQ ID NO:12)) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5ΔHIII vector that was digested with XbaI (partially) and MunI generating pBS.Eco-Eco/ad5ΔHIII.Dgp19K. To allow insertion of foreign genes into the HindIII and BamHI site, an XbaI deletion was made in pBS.Eco-Eco/ad5ΔHIII.Δgp19K to remove the BamHI site in the Bluescript polylinker. The resulting plasmid pBS.Eco-Eco/ad5ΔHIIIΔgp19KΔXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is recloned into pBS.Eco-Eco/ad5ΔHIII.Δgp19K using HindIII and for example MunI. Using this procedure, we have generated plasmids expressing HSV-TK, hIL-1a, rat IL-3, luciferase or LacZ. The unique SrfI and NotI sites in the pBS.Eco-Eco/ad5ΔHIII.Δgp19K plasmid (with or without inserted gene of interest) are used to transfer the region comprising the gene of interest into the corresponding region of pBr/Ad.Bam-rITR, yielding construct pBr/Ad.Bam-rITRΔgp 19K (with or without inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure as described above for E1-replacement vectors using a plasmid-based system consisting of:
a) an adapter plasmid for E1 replacement according to the invention, with or without insertion of a first gene of interest,
b) the pWE/Ad.AflII-EcoRI fragment, and
c) the pBr/Ad.Bam-rITRΔgp19K plasmid with or without insertion of a second gene of interest.

In addition to manipulations in the E3 region, changes of (parts of) the E4 region can be accomplished easily in pBr/Ad.Bam-rITR. Generation and propagation of such a virus, however, in some cases demands complementation in trans.

Example II

Generation of Ad5 Based Viruses with Chimeric Fiber Proteins

The method described infra to generate recombinant adenoviruses by co-transfection of two, or more seperate cloned adenovirus sequences. One of these cloned adenovirus sequences was modified such that the Ad5 fiber DNA was deleted and substituted for unique restriction sites thereby generating "template clones" which allow for the easy introduction of DNA sequences encoding for fiber protein derived from other adenovirus serotypes.

Generation of Adenovirus Template Clones Lacking DNA Encoding for Fiber

The fiber coding sequence of Ad5 is located between nucleotides 31042 and 32787. To remove the Ad5 DNA encoding fiber we started with construct pBr/Ad.Bam-rITR. First a NdeI site was removed from this construct. For this purpose, pBr322 plasmid DNA was digested with NdeI after which protruding ends were filled using Klenow enzyme. This pBr322 plasmid was then re-ligated, digested with NdeI and transformed into *E. coli* DH5a. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRΔNdeI which hence contained a unique NdeI site. Next a PCR was performed with oligonucleotides NY-up: 5'-CGA CAT ATG TAG ATG CAT TAG TTT GTG TTA TGT TTC AAC GTG-3' (SEQ ID NO:13) and NY-down: 5'-GGA GAC CAC TGC CAT GTT-3' (SEQ ID NO:14). During amplification, both a NdeI (bold face) and a NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM $MgCl_2$, and 1 unit of Elongase heat stable polymerase (Gibco, The Netherlands). One-tenth of the PCR product was run on an agarose gel which demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI digested pBr/Ad.Bam-rITRΔNdeI, generating pBr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflIII-EcoRI digested with PacI and EcoRI and a pBr/Ad.BamRΔFib construct in which heterologous fiber sequences have been inserted. To increase the efficiency of virus generation, the construct pBr/Ad.BamRΔFib was modified to generate a PacI site flanking the right ITR. Hereto, pBr/Ad.BamRΔFib was digested with AvrII and the 5 kb adenofragment was isolated and introduced into the vector pBr/Ad.Bam-rITR.pac#8 replacing the corresponding AvrII fragment. The resulting construct was named pBr/Ad.BamRΔFib.pac. Once a heterologous fiber sequence is introduced in pBr/Ad.BamRΔFib.pac, the fiber modified right hand adenovirus clone may be introduced into a large cosmid clone as described for pWE/Ad.AflIII-rITR in Example I. Such a large cosmid clone allows generation of adenovirus by only one homologous recombination making the process extremely efficient.

Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding for fiber protein of alternative serotypes were aligned to identify conserved regions in both the tail-region as well as the knob-region of the fiber protein. From the alignment, which contained the nucleotide sequence of 19 different serotypes representing all 6 subgroups, (degenerate) oligonucleotides were synthesised. The amplification reaction (50 ml) contained 2 mM dNTPs, 25 pmol of each oligonucleotide, standard 1×PCR buffer, 1,5 mM $MgCl_2$, and 1 Unit Pwo heat stable polymerase (Boehringer) per reaction. The cycler program contained 20 cycles, each consisting of 30 sec. 94° C., 60 sec. 60–64° C., and 120 sec. At 72° C. One-tenth of the PCR product was run on an agarose gel which demonstrated that a DNA fragment was amplified. Of each different template, two independent PCR reactions were performed after which the independent PCR fragments obtained were sequenced to determine the nucleotide sequence. From 11 different serotypes, the nucleotide sequence could be compared to sequences present in genbank. Of all other serotypes, the DNA encoding fiber protein was previously unknown and was therefore aligned with known sequences from other subgroup members to determine homology i.e. sequence divergence. Of the 51 human serotypes known to date, all fiber sequences, except for serotypes 1, 6, 18, and 26, have been amplified and sequenced.

Generation of Fiber Chimeric Adenoviral DNA Constructs

All amplified fiber DNAs as well as the vector (pBr/Ad.BamRΔFib) were digested with NdeI and NsiI. The digested DNAs was subsequently run on a agarose gel after which the fragments were isolated from the gel and purified using the Geneclean kit (Bio101 Inc). The PCR fragments were then cloned into the NdeI and NsiI sites of pBr/AdBamRΔFib, thus generating pBr/AdBamRFibXX (where XX stands for the serotype number of which the fiber DNA was isolated). So far the fiber sequence of serotypes 5/ 7/ 8/ 9/ 10/ 11/ 12/ 13/ 14/ 16/ 17/ 19/ 21/ 24/ 27/ 28/ 29/ 30/ 32/ 33/ 34/ 35/ 36/ 37/ 38/ 40-S/ 40-L/41-S/42/45/ 47/ 49/ 51 have been cloned into pBr/AdBamRFibXX. From pBr/AdBamRFibXX (where XX is 5/ 8/ 9/ 10/ 11/ 13/ 16/ 17/ 24/ 27/ 30/ 32/ 33/ 34/ 35/ 38/ 40-S/40-L/45/ 47/ 49/ 51) a cosmid clone in pWE/Ad.AFIII-rITR (see Example I) was generated to facilitate efficient virus generation. This cosmid cloning resulted in the formation of construct pWE/Ad.AflIII-rITR/FibXX (where XX stands for the serotype number of which the fiber DNA was isolated).

Generation of Recombinant Adenovirus Chimeric for Fiber Protein

To generate recombinant Ad 5virus carrying the fiber of serotype 12, 16, 28, 40-L, 51, and 5, three constructs, pCLIP/luciferase, pWE/AdAflIII-Eco and pBr/AdBamrITR.pac/fibXX (XX=12, 16, 28, 40-L, 51, and 5) were transfected into adenovirus producer cells. To generate recombinant Ad5 virus carrying the fiber of5/ 7/ 8/ 9/ 10/ 11/ 12/ 13/ 14/ 16/ 17/ 19/ 21/ 24/ 27/ 28/ 29/ 30/ 32/ 33/ 34/ 35/ 36/ 37 /38/ 40-S/ 40-L/41-S/42/45/47/49/51, two constructs pCLIP/luciferase and pWE/Ad.AflIII-rITR/FibXX were transfected into adenovirus producer cells.

For transfection, 2 µg of pCLIP/luciferase, and 4 µg of both pWE/AdAflIII-Eco and pBr/AdBamrITR.pac/fibXX (or in case of cosmids: 4 µg of pCLIP/luciferase plus 4 µg of pWE/Ad.AflIII-rITR/FibXX) were diluted in serum free DMEM to 100 µl total volume. To this DNA suspension 100 µl 1× diluted lipofectamine (Gibco) was added. After 30 minutes at room temperature the DNA-lipofectamine complex solution was added to 2.5 ml of serum-free DMEM which was subsequently added to a T25 $cm^2$ tissue culture flask. This flask contained 2×10⁶ PER.C6 cells that were seeded 24-hours prior to transfection. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6–8 days, subsequently harvested, and freeze/thawed 3 times. Cellular debris was removed by centrifugation for 5 minutes at 3000 rpm room temperature. Of the supernatant (12.5 ml) 3–5 ml was used to infect again infect PER.C6 cells (T80 cm$^2$ tissue culture flasks). This re-infection results in full cytopathogenic effect (CPE) after 5–6 days after which the adenovirus is harvested as described above.

Example III

Production, Purification, and Titration of Fiber Chimeric Adenoviruses

Of the supernatant obtained from transfected PER.C6 cells 10 ml was used to inoculate a 1 liter fermentor which contained 1–1.5×10$^6$ cells/ml PER.C6 that were specifically adapted to grow in suspension. Three days after inoculation, the cells were harvested and pelleted by centrifugating for 10 min at 1750 rpm at room temperature. The chimeric adenoviruses present in the pelleted cells were subsequently extracted and purified using the following downstream procesing protocol. The pellet was dissolved in 50 ml 10 mM NaPO$_4^-$ and frozen at −20° C. After thawing at 37° C., 5.6 ml deoxycolate (5% w/v) was added after which the solution was homogenated. The solution was subsequently incubated for 15 minutes at 37° C. to completely crack the cells. After homogenizing the solution, 1875 μl (1M) MgCl$_2^-$ was added and 5 ml 100% glycerol. After the addition of 375 μl DNAse (10 mg/ml) the solution was incubated for 30 minutes at 37° C. Cell debris was removed by centrifugation at 1880×g for 30 minutes at room temperature without the brake on. The supernatant was subsequently purified from proteins by loading on 10 ml of freon. Upon centrifugation for 15 minutes at 2000 rpm without brake at room temperature, three bands are visible of which the upper band represents the adenovirus. This band was isolated by pipetting after which it was loaded on a Tris/HCl (1M) buffered caesium chloride blockgradient (range: 1.2 to 1.4 gr./ml). Upon centrifugation at 21000 rpm for 2.5 hours at 10° C., the virus was purified from remaining protein and celldebri since the virus, in contrast to the other components, does not migrate into the 1.4 gr./ml caesium chloride solution. The virus band is isolated after which a second purification using a Tris/HCl (1M) buffered continues gradient of 1.33 gr./ml of caesium chloride is performed. After virus loading on top of this gradient the virus is centrifuged for 17 hours at 55000 rpm at 10° C. Subsequently the virus band is isolated and after the addition of 30 μl of sucrose (50 w/v) excess caesium chloride is removed by three rounds of dialysis, each round comprising of 1 hour. For dialysis the virus is transferred to dialysis slides (Slide-a-lizer, cut off 10000 kDa, Pierce, USA). The buffers used for dialysis are PBS which are supplemented with an increasing concentration of sucrose (round 1 to 3: 30 ml, 60 ml, and 150 ml sucrose (50% w/v)/1.5 liter PBS, all supplemented with 7.5 ml 2% (w/v) CaMgCl$_2$). After dialysis, the virus is removed from the Slide-a-lizer after which it is aliquoted in portions of 25 and 100 μl upon which the virus is stored at −85° C.

To determine the number of virus particles per ml, 100 μl of the virus batch is run on a high pressure liquid chromatograph ("HPLC"). The adenovirus is bound to the column (anion exchange) after which it is eluted using a NaCl gradient (range 300–600 mM). By determining the area under the virus peak the number of virus particles can be calculated. To determine the number of infectious units (IU) per ml present in a virus batch, titrations are performed on 911 cells. For this purpose, 4×10$^4$ 911 cells are seeded per well of 96-well plates in rows B, D, and F in a total volume of 100 μl per well. Three hours after seeding the cells are attached to the plastic support after which the medium can be removed. To the cells, a volume of 200 μl is added, in duplicate, containing different dilutions of virus (range: 10$^2$ times diluted to 2×10$^9$). By screening for CPE the highest virus dilution which still renders CPE after 14 days is considered to contain at least one infectious unit. Using this observation, together with the calculated amount of virus volume present in these wells renders the number of infectious units per ml of a given virus batch. The production results i.e. virus particles per ml and IU per ml or those chimeric adenoviruses that were produced, all with the luciferase cDNA as a marker, are shown in Table 2.

Example IV

Transduction of Human Mesenchymal Stem Cells

The adherent fraction derived from a bone marrow aspirate obtained from a healthy donor was cultured in Dulbecco's modified Eagle's medium (DMEM) supplemented with D-glucose (1 gr/liter), sodium pyruvate and sodium bicarbonate (4.4 g/l), L-glutamine (2 mM), penicillin (100 U/ml), streptomycin (100 μg/ml), and 10% heat inactivated fetal calf serum. Cells were passaged in a 1:2 ratio upon reaching confluency. For transduction, cells were seeded at a concentration of 5×10$^4$ cells per well of 24-well plates, and allowed to adhere for 24 hours. Cells were subsequently exposed to 1000 virus particles per cell of Ad5 or the fiber chimeric viruses Ad5.Fib12, Ad5.Fib16, Ad5.Fib35, Ad5.Fib40-S, Ad5Fib40-L, Ad5.Fib45, or Ad5.Fib51. The fibers 40-S and 40-L represent the short and the long fiber of serotype 40 respectively. Forty-eight hours after virus addition cells were harvested, and lysed by addition of 100 μl of cell-lysis buffer (PBS/1% Triton-X100). Luciferase activity was determined using a bioluminescence machine, the luciferase assay kit from Promega™ (catalog no. E-1501) and the instructions provided by the manufacturer. The results of the luciferase transgene expression measured in mesenchymal stem cells after transduction with the panel of fiber chimeric viruses is shown in FIG. 1. The results demonstrate that several fiber chimeric viruses perform better on fibroblasts as compared to the parent vector (Ad5). These viruses carry the fiber from a subgroup B virus i.e. 16, 35, and 51. Also, one subgroup D virus (Ad5.Fib32) seems better equipped for transducing mesenchymal stem cells. Both Ad5.Fib40-S and Ad5.Fib40-L (subgroup F) perform similar or only slightly better as compared to Ad5.

Figure 2:
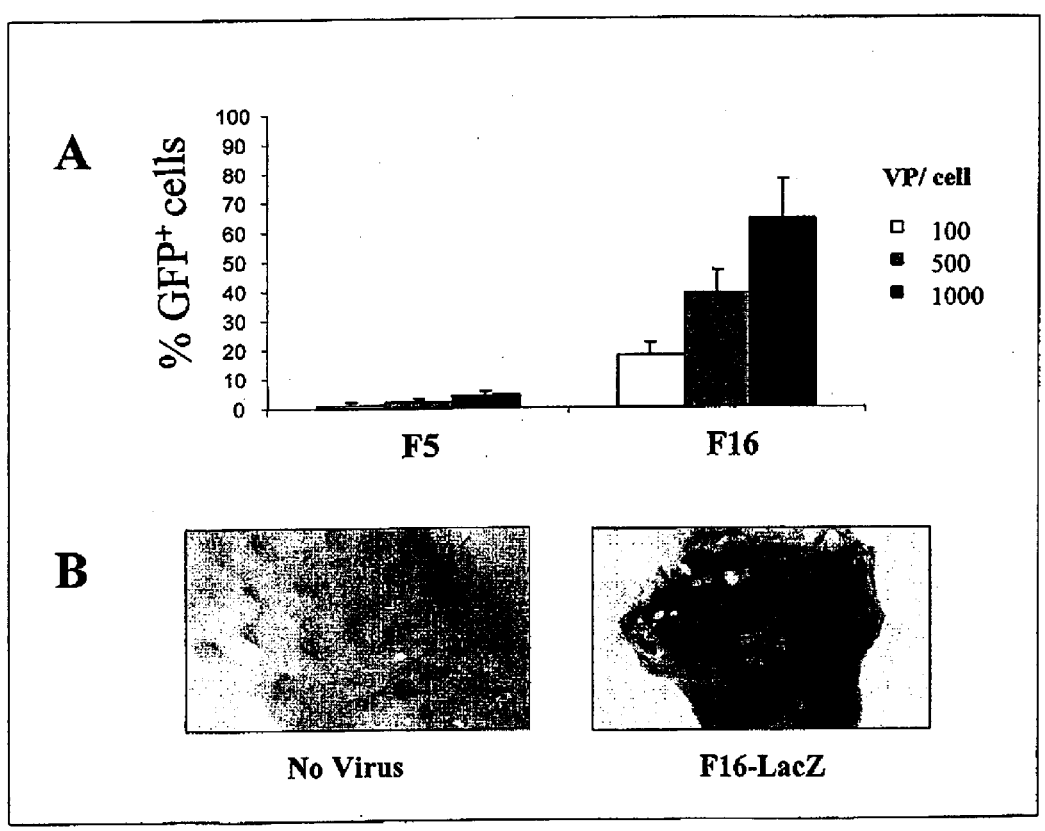
FIG. 2: Transduction of Human bone marrow stroma cells ("MSCs") with Ad5.Fib16. (A): HBSCs were exposed for one hour to 100, 500, or 1000 virus particles of Ad5 or Ad5.Fib16. Forty-eight hours later cells were screened using a flow cytometer for the expression of GFP. Shown is the average ± standard deviation percentage of cells that are positive for GFP (N=3). (B) HBSCs were exposed to 5000 virus particles per cell and seeded in a polymeric scaffold. Forty-eight hours after virus exposure the cells were stained for LacZ expression. As a control for the LacZ staining reaction, non-transduced cells (no virus) were taken along.
Figure 3:
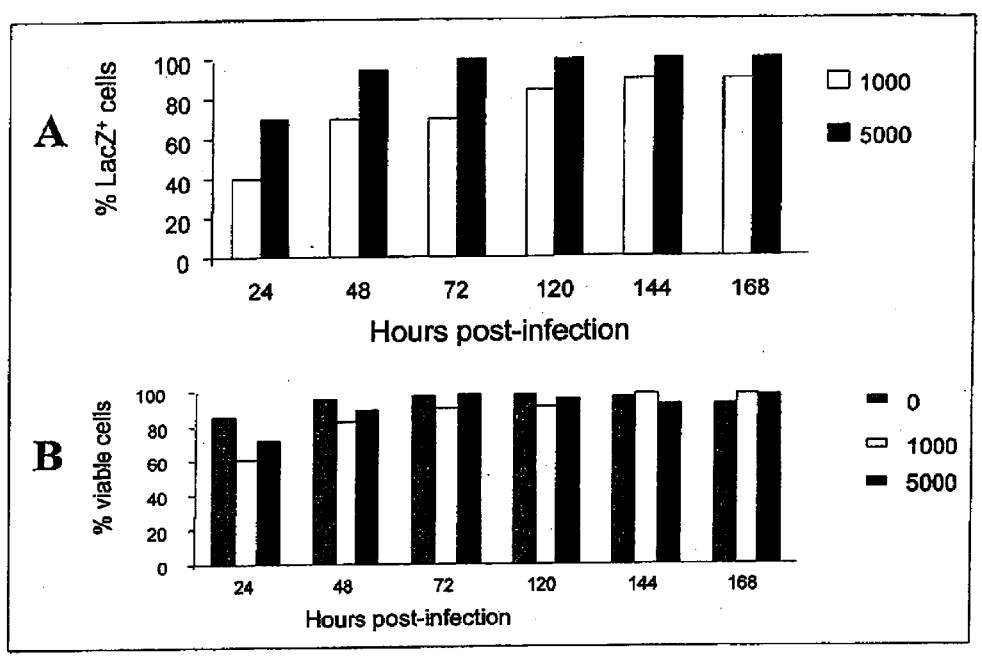
FIG. 3: duration of marker gene expression and toxicity of Ad5Fib16 on mesenchymal stem cells. (A) HBSCs were exposed for one hour to 1000 or 5000 virus particles per cell of Ad5Fib16 lacZ. Cells were stained for LacZ expression at different time points after virus exposure. (B) Cells were infected for one hour with 1000 or 5000 virus particles. At different time points after exposure to Ad5Fib16 cells were harvested and the viability of the cell population was determined. As a control, cells not exposed (0) to virus were taken along.

In a next experiment, we tested the ability of Ad5Fib16 carrying other marker genes to infect mesenchymal stem cells. Hereto, the cells were exposed for two hours to an increasing vector dose of A5 or Ad5Fib16 carrying green fluorescent protein as a marker (FIG. 2a). Forty-eight hours later cells were harvested, and using a flow cytometer, the cells were tested for GFP expression. The results obtained demonstrated that, based on the percentage of cells positive for the marker gene, Ad5.Fib16 is much more potent compared to Ad5 for the genetic modification of mesenchymal stem cells. Also, mesenchymal stem cells were seeded in a biodegradable polymeric scafolld and cells were exposed to Ad5.Fib16 carrying LacZ as a marker gene. Again 48 hours later, cells were stained for LacZ expression (FIG. 2b). Clearly, the cells stained blue after transduction with Ad5.Fib16 again showing the efficiency by which Ad5.Fib16 infects mesenchymal stem cells. Finally, we tested the expression of a marker gene over time to investigate the duration of expression. Hereto, HBSCs were exposed for one hour to 1000 or 500 virus particles per cell of Ad5.Fib16 carrying LacZ. The number of cells scored positive for LacZ was monitored at 24, 48, 72, 120, 144, and 168 hours after the one hour virus exposure. With a dose of 5000 virus particles per cell, all cells were infected since 100% of the cells stained positive for LacZ at 48 hours after virus exposure (FIG. 3a). Generally the time required to obtain optimal expression after infection is 48 hours. Since the number of LacZ positive cells remained at 100% for all time points tested, i.e., until 168 hours after infection it can be concluded that each cell nucleus contains at least 4 copies of the Ad5Fib16 genome since 4 cell doublings did not dilute out the virus. In the latter experiment we also monitored the viability of the transduced cells either infected with 1000 or 5000 virus particles per cell.

As control, non-transduced cells were analyzed. Based on the percentage of viable cells after transduction with Ad5Fib16, it can be concluded that even a dose of 5000 virus particles per cell does not significantly change the cellular viability. All together these results show that the improved vectors identified are extremly potent to infect Human bone marrow stroma cells or mesenchymal stem cells without compromising the cellular viability. These results thus pave the road to start studies aimed at optimizing the quantity and quality of bio-artificial engineered bone.

REFERENCES

Arnberg N., Mei Y. and Wadell G., 1997. Fiber genes of adenoviruses with tropism for the eye and the genital tract. Virology 227: 239–244.

Bjornson, C. R., Rietze, R. L., Reynolds, B. A., Magli, M. C., Vescovi, A. L. (1999) Turning brain into blood: a hematopoietic fate adopted by adult neural stem cells in vivo. Science 283, p534–537.

Boden, S. D., Viggeswarapu, M., Liu, Y., Hair, G. A., Ugbo, J. L., titus, L. (2000). Adenoviral delivery of LIM mineralization protein 1 succesfully induces de novo bone formation in vivo. Abstract 204 Keystone symposia Januari 6–12 Keystone Resort Colorado USA.

Bout, A. (1996) Prospects for human gene therapy. Eur. J. Drug Met. and Pharma. 2, 175–179.

Blaese, M., Blankenstein, T., Brenner, M., Cohen-Hagenauer, O., Gansbacher, B., Russel, S., Sorrentino, B. and Velu, T. (1995) Cancer Gene Ther. 2: 291–297.

Brody, S. L. and Crystal, R. G. (1994) Adenovirus mediated in vivo gene transfer. Ann. N. Y. Acad. Sci. 716:90–101.

Bruder, S. P., Fink, D. J., Caplan, A. I. (1994) Mesenchymal stem cells in bone development, bone repair, and skeletal regeneration therapy. J. Cell. Biochem. 56: p283–294.

Chen, S-J., Wilson, J. M., Vallance, D. K., Hartman, J. W., Davidson, B. L. Roessler, B. J.(1995) A recombinant adenoviral vector expressing a soluble form of VCAM-1 inhibits VCAM-1/VLA-4 adhesion in transduced synoviocytes. Gene Ther. 2, p469–480.

Chroboczek J., Ruigrok R. W. H., and Cusack S., 1995. Adenovirus fiber, p.163–200. In: W. Doerfler and P. Bohm (ed.), The molecular repertoire of adenoviruses, I. Springer-Verlag, Berlin.

Conçalves, M. A. F. V.; Pau, M. G.; Valerio D.; de Vries, A. A. F. (2000). Prolonged transgene expression provided by a high-capacity adeno-associated virus/adenovirus hybrid vector. Molecular Therapy Vol. 1 (No. 5), abstract 351, p137.

Crosbie O. M., Reynolds, M., McEntee, G., Traynor, O., Hegarthy, J. E., O"Farrelly, C. (1999) In vitro evidence for the presence of hematopoietic stem cells in the adult human liver. Hepatology 29, p1193–1198.

Dechanet J., Merville P., Durand I., Banchereau J., Miossec P. (1995) The ability of synoviocytes to support terminal differentiation of activated B cells may explain plasma cell accumulation in rheumatoid synovium. J Clin Invest 95, p456–463.

Defer C., Belin M., Caillet-Boudin M. and Boulanger P., 1990. Human adenovirus-host cell interactions; comparative study with members of subgroup B and C. Journal of Virology 64 (8): 3661–3673.

De Jong J. C., Wermenbol A. G., Verweij-Uijterwaal M. W., Slaterus K. W., Wertheim-Van Dillen P., Van Doornum G. J., Khoo S. H., Hierholzer J. C. (1999) Adenoviruses from human immunodeficiency virus-infected individuals, including two strains that represent new candidate serotypes Ad50 and Ad51of species B1 and D, respectively. J Clin Microbiol 37: pp. 3940–3945.

Feng, M.; Jacksin, W. H.; Goldman, C. K.; Rancourt C.; Wang M.; Dusing, S. K.; Siegal, G; Curiel, D. T. (1997). Stable in vivo gene transduction via a novel adenoviral/retroviral chimeric vector. Nature Biotechnology, vol. 15, pp. 866–870.

Francki, R. I. B., Fauquet, C. M., Knudson, D. L. and Brown, F. (1991) Classification and nomenclature of viruses. Fifth report of the international Committee on taxonomy of viruses. Arch. Virol. Suppl. 2:140–144.

Goldberg, V. M. and Caplan, A. I. (1994) Biological resurfacing: an alternative to total joint arthroplasty. Othopedics 17: p819–821.

Greber, U. F., Willets, M., Webster, P., and Helenius, A. (1993). Stepwise dismanteling of adenovirus 2 during entry into cells. Cell 75: 477–486.

Hierholzer, J. C. (1992) Adenovirus in the immunocompromised host. Clin. Microbiol Rev. 5: 262–274.

Hierholzer, J. C., Wigand, R., Anderson, L. J., Adrian, T., and Gold, J. W. M. (1988) Adenoviruses from patients with AIDS: a plethora of serotypes and a description of five new serotypes of subgenus D (types 43-47). J. Infect. Dis. 158: 804–813.

Hynes, R. O. (1992) Integrins: versatility, modulation and signalling in cell adhesion. Cell 69: 11–25.

Ishibashi, M. and Yasue, H. (1984) The adenoviruses, H. S. Ginsberg, ed., Plenum Press, London, New York. Chapter 12, 497–561.

Jackson, K. A., Mi, T., Goodell, M. A. (1999). Hemopoietic potenytial of stem cells isolated from murine skeletal muscle. Proc. Natl. Acad. Sci (USA) 96: p14482–14486.

Khoo, S. H., Bailey, A. S., De Jong, J. C., and Mandal, B. K. (1995). Adenovirus infections in human immunodeficiency virus-positive patients: Clinical features and molecular epidemiology. J. Infect. Dis 172: 629–637

Kidd, A. H., Chroboczek, J., Cusack, S., and Ruigrok, R. W. (1993) Adenovirus type 40 virions contain two distinct fibers. Virology 192: 73–84.

Krasnykh V. N., Mikheeva G. V., Douglas J. T. and Curiel D. T. (1996) Generation of recombinant adenovirus vectors with modified fibers for altering viral tropism. J. Virol. 70(10): 6839–6846.

Krasnykh V. N., Dmitriev I., Mikheeva G., Miller C. R., Belousova N. and Curiel D. T. (1998) Characterization of an adenovirus vector containing a heterologous peptide epitope in the HI loop of the fiber knob. J. Virol. 72(3): 1844–1852.

Levrero M., Barban V., Manteca S., Ballay A., Balsamo C., Avantaggiati M. L., Natoli G., Skellekens H., Tiollais P., Perricaudet M. (1991) Defective and nondefective adenovirus vectors for expressing foreign genes in vitro and in vivo. Gene 101: p195–202.

Lou, J., Xu, F., Merkel, K. Manske, P. (1999). Gene therapy: adenovirus mediated human bone morphogenesis protein-2 gene transfer induces mesenchymal progenitor cell proliferation and differentiation in vitro and bone formation in vivo. J. Orthop. Res. 17, p43–50

Morgan, C., Rozenkrantz, H. S., and Mednis, B. (1969) Structure and development of viruses as observed in the electron microscope X. Entry and uncoating of adenovirus. J. Virol 4, 777–796.

Prockop, D. J. (1997) Marrow stromal cells as stem cells for nonhematopoietic tissues. Science 276: p71–74.

Roelvink, P. W., Lizonova, A., Lee, J. G. M., Li, Y., Bergelson, J. M., Finberg, R. W., Brough, D. E., Kovesdi, I. and Wickham, T. J. (1998) The coxsackie-adenovirus receptor protein can function as a cellular attachment protein for adenovirus serotypes from subgroups A, C, D, E, and F. J. Virol. 72: p7909–7915.

Schnurr, D and Dondero, M. E. (1993) Two new candidate adenovirus serotypes. Intervirol. 36: p79–83.

Signas, G., Akusjarvi, G., and Petterson, U. (1985). Adenovirus 3 fiber polypeptide gene: Complications for the structure of the fiber protein. J. Virol. 53: p672–678.

Stevenson S. C., Rollence M., White B., Weaver L. and McClelland A. (1995) Human adenovirus serotypes 3 and 5 bind to two different cellular receptors via the fiber head domain. J. Virol 69(5): 2850–2857.

Stevenson S. C., Rollence M., Marshall-Neff J. and McClelland A. (1997) Selective targeting of human cells by a chimeric adenovirus vector containing a modified fiber protein. J. Virology 71(6): 4782–4790.

Stouten, P. W. F., Sander, C., Ruigrok, R. W. H., and Cusack, S. (1992) New triple helical model for the shaft of the adenovirus fiber. J. Mol. Biol. 226, 1073–1084.

Svensson, V. and Persson, R. (1984). Entry of adenovirus 2 into Hela cells. J. Virol. 51,687-694.

Varga, M. J., Weibull, C., and Everitt, E. (1991). Infectious entry pathway of adenovirus type 2. J. Virol 65, 6061–6070.

Wakitani S, Goto T, Pineda S J, Young R G, Mansour J M, Caplan A I, Goldberg V M. (1994) Mesenchymal cell-based repair of large, full-thickness defects of articular cartilage. J Bone Joint Surg Am 76: p579–592.

Wickham T. J., Carrion M. E. and Kovesdi I., 1995. Targeting of adenovirus penton base to new receptors through replacement of its RGD motif with other receptor-specific peptide motifs. Gene Therapy 2: 750–756.

Wickham, T. J., Mathias, P., Cherish, D. A., and Nemerow, G. R. (1993) Integrins avb3 and avb5 promote adenovirus internalization but not virus attachment. Cell 73, 309–319.

Zheng, Changyu; Baum, B. J.; Ladorala, M. J.; O"Conell, B. C. (2000. Genomic integration and gene expression by a modified adenoviral vector. Nature, vol 18, p176–180.

TABLE 1

Association of different human adenovirus serotypes with human disease.

| Syndrome | Subgenus | Serotype |
| --- | --- | --- |
| Respiratory illness | A | 31 |
| | B | 3, 7, 11, 14, 21, 34, 35, 51 |
| | C | 1, 2, 5, 6 |
| | D | 39, 42–48 |
| | E | 4 |
| Keratoconjunctivitis (eye) | B | 11 |
| | D | 8, 19, 37, 50 |
| Hemorrhagic cystitis (Kidney) | B | 7, 11, 14, 16, 21, 34, 35 |
| And urogenital tract infections | C | 5 |
| | D | 39, 42–48 |
| Sexual transmission | C | 2 |
| | D | 19, 37 |
| Gastroenteritis | A | 31 |
| | B | 3 |
| | C | 1, 2, 5 |
| | D | 28 |
| | F | 40, 41 |
| CNS disease | A | 12, 31 |
| | B | 3, 7 |
| | C | 2, 5, 6 |
| | D | 32, 49 |
| Hepatitis | A | 31 |
| | C | 1, 2, 5 |
| Disseminated | A | 31 |
| | B | 3, 7, 11, 21 |
| | D | 30, 43–47 |
| None (???) | A | 18 |
| | D | 9, 10, 13, 15 17, 20, 22–29, 33, 36, 38 |

TABLE 2

Production results of recombinant fiber chimeric adenoviruses.
Results in virus particles per milliliter as determined by HPLC.

| Adenovirus | Virus particles/ml |
| --- | --- |
| Ad5Fib5 | $2.2 \times 10^{12}$ |
| Ad5Fib9 | $4.9 \times 10^{11}$ |
| Ad5Fib10 | $5.5 \times 10^{11}$ |
| Ad5Fib11 | $1.1 \times 10^{12}$ |
| Ad5Fib12 | $4.4 \times 10^{12}$ |
| Ad5Fib13 | $1.1 \times 10^{12}$ |
| Ad5Fib16 | $1.4 \times 10^{12}$ |
| Ad5Fib17 | $9.3 \times 10^{11}$ |
| Ad5Fib24 | $1.0 \times 10^{12}$ |
| Ad5Fib27 | $3.0 \times 10^{11}$ |
| Ad5Fib30 | $7.1 \times 10^{11}$ |
| Ad5Fib32 | $2.0 \times 10^{12}$ |
| Ad5Fib33 | $1.5 \times 10^{12}$ |
| Ad5Fib35 | $2.0 \times 10^{12}$ |
| Ad5Fib38 | $5.8 \times 10^{11}$ |
| Ad5Fib40-S | $3.2 \times 10^{10}$ |
| Ad5Fib40-L | $2.0 \times 10^{12}$ |
| Ad5Fib45 | $2.8 \times 10^{12}$ |
| Ad5Fib47 | $2.6 \times 10^{12}$ |
| Ad5Fib49 | $1.2 \times 10^{12}$ |
| Ad5Fib51 | $5.1 \times 10^{12}$ |

What is claimed is:

1. A method for delivering a nucleic acid of interest to a mesenchymal stem cell, said method comprising:
   culturing a mesenchymal stem cell in vitro; and
   infecting the mesenchymal stem cell, in vitro, with a recombinant adenovirus of subgroup C, said recombinant adenovirus comprising the nucleic acid of interest and further comprising a fiber protein of a second adenovirus serotype the recombinant adenovirus capsid, wherein the fiber protein provides a tissue tropism for mesenchymal stem cells and the second adenovirus serotype is selected from the group consisting of serotype 16, serotype 32, serotype 35, serotype 40-S, and serotype 51.

2. The method according to claim 1, wherein said adenovirus serotype of subgroup C is adenovirus serotype 5.

3. The method according to claim 1, wherein the second adenovirus serotype is serotype 16.

4. The method according to claim 1, wherein the second adenovirus serotype is serotype 35.

5. A method for delivering a nucleic acid of interest to a mesenchymal stem cell in vitro, said method comprising:
   culturing the mesenchymal stem cell in vitro; and
   infecting the mesenchymal stem cell in vitro with a recombinant adenovirus of subgroup C, said recombinant adenovirus comprising a nucleic acid of interest and further comprising a fiber protein in its capsid, wherein the fiber protein comprises a knob of a fiber protein from an adenovirus serotype selected from the group consisting of serotype 16, serotype 32, serotype 35, serotype 40-S, and serotype 51, wherein the knob provides the recombinant adenovirus with the tropism for the mesenchymal stem cell.

6. The method according to claim 5, wherein said adenovirus serotype of subgroup C is adenovirus serotype 5.

7. The method according to claim 5, wherein the fiber protein is serotype 16.

8. The method according to claim 5, wherein the fiber protein is serotype 35.

9. The method according to claim 5, wherein the knob is from adenovirus serotype 35.

10. The method according to claim 5, wherein the knob is from adenovirus serotype 16.

11. The method according to claim 6, wherein the fiber protein comprises a tail of adenovirus serotype 5.

12. The method according to claim 11, wherein the knob is from adenovirus serotype 16.

* * * * *

UNITED STATES PATENT AND TRADEMARK OFFICE
CERTIFICATE OF CORRECTION

PATENT NO. : 6,905,678 B2  
APPLICATION NO. : 10/010645  
DATED : June 14, 2005  
INVENTOR(S) : Menzo Jans Emco Havenga, Abraham Bout and Ronald Vogels It is certified that error appears in the above-identified patent and that said Letters Patent is hereby corrected as shown below:

On the title page:
In ITEM (56) References Cited   Page 2, Col. 1, Line 3, change "Adenovisidae,"" to --Adenoviridae,"-- Page 2, Col. 2, Line 9, change "modified adenovrus," to --modified adenovirus,--

In the specification:
- COLUMN 13, LINE 7, change "Ad.AfIII" to --Ad.AflII--
- COLUMN 13, LINE 17, change "pBr/Ad.AFIII" to --pBr/Ad.AflII--
- COLUMN 13, LINE 35, change "AFIII-" to --AflII- --
- COLUMN 14, LINE 52, change "pWE/Ad.AfIII-EcoRI" to --pWE/Ad.AflII-EcoRI--
- COLUMN 15, LINE 21, change "5'-CGA CAT ATG TAG" to --5'-CGA CAT ATG TAG--
- COLUMN 20, LINE 23, change "Ad51of" to --Ad51 of--

Signed and Sealed this

Sixteenth Day of December, 2008

JON W. DUDAS  
*Director of the United States Patent and Trademark Office*

SEQUENCE LISTING

<160> NUMBER OF SEQ ID NOS: 14

<210> SEQ ID NO 1
<211> LENGTH: 6
<212> TYPE: PRT
<213> ORGANISM: Adenovirus

<400> SEQUENCE: 1

Phe Asn Pro Val Tyr Pro
1               5

<210> SEQ ID NO 2
<211> LENGTH: 23
<212> TYPE: DNA
<213> ORGANISM: Artificial Sequence
<220> FEATURE:
<223> OTHER INFORMATION: oligo linker

<400> SEQUENCE: 2
aattgtctta attaaccgct taa                                              23

<210> SEQ ID NO 3
<211> LENGTH: 19
<212> TYPE: DNA
<213> ORGANISM: Artificial Sequence
<220> FEATURE:
<223> OTHER INFORMATION: oligonucleotide

<400> SEQUENCE: 3
aattgtctta attaaccgc                                                   19

<210> SEQ ID NO 4
<211> LENGTH: 19
<212> TYPE: DNA
<213> ORGANISM: Artificial Sequence
<220> FEATURE:
<223> OTHER INFORMATION: oligonucleotide

<400> SEQUENCE: 4
aattgcggtt aattaagac                                                   19

<210> SEQ ID NO 5
<211> LENGTH: 47
<212> TYPE: DNA
<213> ORGANISM: Artificial Sequence
<220> FEATURE:
<223> OTHER INFORMATION: primer

<400> SEQUENCE: 5
ctgtacgtac cagtgcactg gcctaggcat ggaaaaatac ataactg                    47

<210> SEQ ID NO 6
<211> LENGTH: 64
<212> TYPE: DNA
<213> ORGANISM: Artificial Sequence
<220> FEATURE:
<223> OTHER INFORMATION: primer

<400> SEQUENCE: 6
gcggatcctt cgaaccatgg taagcttggt accgctagcg ttaaccgggc gactcagtca      60
atcg                                                                  64

<210> SEQ ID NO 7

```
<211> LENGTH: 28
<212> TYPE: DNA
<213> ORGANISM: Artificial Sequence
<220> FEATURE:
<223> OTHER INFORMATION: primer

<400> SEQUENCE: 7
gcgccaccat gggcagagcg atggtggc                                      28

<210> SEQ ID NO 8
<211> LENGTH: 50
<212> TYPE: DNA
<213> ORGANISM: Artificial Sequence
<220> FEATURE:
<223> OTHER INFORMATION: primer

<400> SEQUENCE: 8
gttagatcta agcttgtcga catcgatcta ctaacagtag agatgtagaa              50

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gggtattagg ccaaaggcgc a                                             21

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
gatcccatgg aagcttgggt ggcgacccca gcg                                33

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gatcccatgg ggatccttta ctaagttaca aagcta                             36

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gtcgctgtag ttggactgg                                                19

<210> SEQ ID NO 13
<211> LENGTH: 42
<212> TYPE: DNA
<213> ORGANISM: Artificial Sequence
<220> FEATURE:
<223> OTHER INFORMATION: oligonucleotide

<400> SEQUENCE: 13
```

```
cgacatatgt agatgcatta gtttgtgtta tgtttcaacg tg                          42
```

<210> SEQ ID NO 14
<211> LENGTH: 18
<212> TYPE: DNA
<213> ORGANISM: Artificial Sequence
<220> FEATURE:
<223> OTHER INFORMATION: oligonucleotide

<400> SEQUENCE: 14

```
ggagaccact gccatgtt                                                     18
```